United States Patent [19]

Harako

[11] Patent Number: 5,443,990
[45] Date of Patent: Aug. 22, 1995

[54] COMPOSITION FOR MEASURING IONIC STRENGTH OR SPECIFIC GRAVITY OF LIQUID SPECIMEN AND TEST PIECE PREPARED FROM SAID COMPOSITION

[75] Inventor: Mieko Harako, Ichikawa, Japan

[73] Assignee: Eiken Kagaku Kabushiki Kaisha, Tokyo, Japan

[21] Appl. No.: 122,570

[22] PCT Filed: Apr. 10, 1992

[86] PCT No.: PCT/JP92/80459

§ 371 Date: Oct. 1, 1993

§ 102(e) Date: Oct. 1, 1993

[87] PCT Pub. No.: WO92/18863

PCT Pub. Date: Oct. 29, 1992

[30] Foreign Application Priority Data

Apr. 11, 1991 [JP] Japan .................... 3-106735

[51] Int. Cl.$^6$ ............... G01N 33/52; G01N 33/48
[52] U.S. Cl. ...................... 436/74; 422/56; 422/57; 422/58; 436/2; 436/164; 436/166; 436/169
[58] Field of Search ............ 422/56, 57, 58, 104; 436/2, 166, 169, 66, 74, 164

[56] References Cited

U.S. PATENT DOCUMENTS

| | | | |
|---|---|---|---|
| 3,856,528 | 12/1974 | Levinos | 96/49 |
| 4,015,462 | 4/1977 | Greyson et al. | 436/166 X |
| 4,076,502 | 2/1978 | Dugle et al. | 195/103.5 C X |
| 4,108,727 | 8/1978 | Stiso | 195/103.5 R X |
| 4,308,215 | 12/1981 | Vaughan | 260/505 |
| 4,318,709 | 3/1982 | Falb et al. | 422/56 |
| 4,376,827 | 3/1983 | Stiso et al. | 422/56 X |
| 4,473,650 | 9/1984 | Wang | 436/169 X |
| 4,532,107 | 7/1985 | Siddigi | 422/56 |
| 4,532,216 | 7/1985 | Wang | 422/56 X |
| 5,089,420 | 2/1992 | Albarella et al. | 436/66 |
| 5,302,531 | 4/1994 | Bauer | 436/74 |
| 5,320,969 | 6/1994 | Bauer et al. | 436/169 X |

FOREIGN PATENT DOCUMENTS

| | | |
|---|---|---|
| 55-101047 | 8/1980 | Japan . |
| 56-21064 | 2/1981 | Japan . |
| 59-112251 | 6/1984 | Japan . |
| 59-120843 | 7/1984 | Japan . |
| 59-160739 | 9/1984 | Japan . |
| 60-46374 | 3/1985 | Japan . |
| 62-12858 | 1/1987 | Japan . |
| 62-95462 | 5/1987 | Japan . |
| 2-66451 | 3/1990 | Japan . |
| 2-73134 | 3/1990 | Japan . |

OTHER PUBLICATIONS

Toei, "Ion–Association Reagents A Review", Analytical Sciences, Dec. 1987, vol. 3, pp. 479–488.
Bunseki, 1989, 1, pp. 61–72.
Bunseki, 1990, pp. 82–86.
Shinkagaku Jikkenkouza 9, Bunseki Kagaku (II) 1977, pp. 556–560.

*Primary Examiner*—Donald E. Czaja
*Assistant Examiner*—Milton I. Cano
*Attorney, Agent, or Firm*—Oliff & Berridge

[57] ABSTRACT

A composition is used to measure the ionic strength or specific gravity of a liquid specimen and a test piece prepared from the composition. The composition is an anion type of ion-associable reagent and a cation type of ion-associable reagent. The composition may also contain a pH buffer agent. The use of the composition and test piece prepared from the composition enable the easy, simple, quick, but exact measurement of ionic strength or specific gravity of a liquid specimen without influence by characteristics of the specimen.

6 Claims, 2 Drawing Sheets

COMPOSITION FOR MEASURING IONIC STRENGTH OR SPECIFIC GRAVITY OF LIQUID SPECIMEN AND TEST PIECE PREPARED FROM SAID COMPOSITION

TECHNICAL FIELD

This invention relates to a composition for measuring the ionic strength or specific gravity of a liquid specimen, and to a test piece prepared by using the composition.

BACKGROUND ART

The measurement of specific gravity of a liquid specimen is employed in a wide variety of technical fields. The measurement of specific gravity of urine is one of the important items of measurement in the field of clinical chemistry. Physical method for measurement using liquid gravimeters, urine gravimeters, pycnometers, refractometers, osmometers, etc. were usually employed for measuring the specific gravity of urine. The instruments used by these methods were, however, expensive and fragile, and their handling called for the utmost care. Moreover, the instruments called for occasional maintenance including cleaning and calibration. Thus, the measurement by any of these physical methods took a great deal of labor and time.

Simpler physical methods for measurement have been proposed. For example, Japanese Patent Application Laid-open No. 120843/1984 discloses a sheet for gravimetric examination formed from a porous resinous material, but a method employing this sheet calls for the strict determination by a spectrophotometer or refractometer of the transmission or refractive index of the sheet impregnated with a liquid to be examined, such as urine. Japanese Patent Application Laid-open No. 112251/1984 discloses a piece for the gravimetric measurement of urine having a gravimetric measuring chamber which holds a plurality of beads differing from one another is specific gravity, but it is too complicated in construction to be easily manufactured.

In the field of clinical chemistry methods relying upon colorimetric analysis by test pieces are employed for carrying out an assay for constituents in a specimen of body fluids, such as urine, at a low cost in a simple and quick operation. The methods relying upon colorimetric analysis are easy to understand and carry out with few errors, insofar as variations in color can be visually recognized. The results are easy to obtain visually, or by a simple device such as a color analyzer. Methods relying upon colorimetric analysis by test pieces for determining the ionic strength, or specific gravity of a liquid specimen have recently been proposed in, for example, Japanese Patent Publication No. 12858/1987, Japanese Patent Laid-open Nos. 160739/1984, 21064/1981, 66451/1990 and 95462/1987, and Japanese Patent Publication No. 46374/1985.

The known method for the colorimetric determination of the ionic strength, or specific gravity of a liquid specimen, as disclosed in the publications referred to above, employed test pieces prepared from, or by using, an electrolytic polymer, a chelate forming agent, a pH buffer agent, a pH indicator, a highly absorbent resin, a microcapsule, etc. It has, however, been difficult to carry out an accurate determination by any of the known methods, since the results thereof are easily affected by the pH or temperature of the liquid specimen, the length of time employed for the determination, etc. Moreover, many of the test pieces employed by those methods are generally difficult to prepare.

This invention is intended for overcoming the drawbacks of the prior art as above pointed out. It is an object of this invention to provide a composition which enables the measurement of ionic strength, or specific gravity of a liquid specimen to be carried out easily, quickly and accurately without being influenced by the characteristics of the specimen, such as its pH and temperature, and a test piece which is easy to prepare by using the composition.

DISCLOSURE OF THE INVENTION

The composition of this invention for measuring the ionic strength or specific gravity of a liquid specimen comprises an ion-associable anion reagent of the ionically associable type and an ion-associable cation reagent of the ionically associable type, and may optionally contain a buffer agent.

The anionic ion-associable anion reagent in the composition of this invention is preferably a polymer or chain compound having a sulfonate, sulfate or phosphate ester group.

The polymer preferred as the anionic ion-associable anion reagent is selected from the group consisting of sodium dextran sulfate, sodium heparinate, sodium chondroitin sulfate, sodium cellulose sulfate and nucleic acid.

The chain compound preferred as the anionic ion-associable reagent is sodium dodecylsulfate or sodium dodecylbenzensulfate. The preferred polymer or chain compound have always single negative change over a wide pH range, since it is a strong electrolyte.

The ion-associable cation in the composition of this invention is preferably a basic dye. It is a dye which does not change color in a pH range of 5 to 7 (the pH range of normal urine).ss The basic dye is preferably selected from the group consisting of thiazine, oxazine, azine, triphenylmethane, diphenylmethane, azo, indoaniline, and aminoindophenol dyes.

The preferred thiazine dye is Methylene Blue.

The preferred oxazlne dye is Brilliant Cresyl Blue, or Nile Blue.

The preferred azine dye is Safranine O.

The preferred triphenylmethane dye is Crystal Violet.

The preferred indoaniline dye is o-Toluidine Blue.

The mixing ratio of the anionic and cationic ion-associable anion and cation reagents depend on the substances used as such and the liquid to be examined.

It is possible to add an appropriate amount of, for example a phosphate, nitrate, carbonate, citrate, diethylmalonate, or a derivative of animoalkylsulfonic acid as the buffer, if required. The pH buffer range is preferably in a pH range of 5 to 10.

The composition of this invention can conveniently be used to impregnate an absorbent carrier to form a test piece having appropriate properties.

The absorbent carrier can be prepared from, for example, paper, cotton, wood a non-woven fabric, a powder, or a hydrophilic polymer. The use of filter paper is, among others, preferred.

The absorbent carrier may itself be used as a test piece, or may alternatively be appropriately sized and shaped, and attached to an appropriate support, for example, a plastic sheet, as of polystyrene, polyvinyl chloride, or polu. It is also possible to use a hydrophllic polymer as an absorbent carrier and adhesive, apply a mixture thereof with the composition of this invention onto a support such as a plastic sheet, and dry it to solidify to make a test piece.

The support may, for example, be colored, or marked with symbols, letters, figures or patterns as desired to facilitate the identification of the results of measurement.

I) Principle of Measurement:

The ionic strength or specific gravity of an aqueous solution is indirectly measured by utilizing the effects which salts exert on the ion-association between ion-associable anion and cation reagents.

II) Explanation of the Principle of Measurement:

The ion-association is the combination of an anion and cation which does not rely upon any coordinate bond (Bunseki, 1989, 1, p61), and the change in color of a dye by an ion-association is called metachromasy (Bunseki, 1990,3, p82). A dye of ion-associable cation changes its electron state, and its color, too, as a result of its ion-association with an ion-associable anion.

A typical combination which causes metachromasy is of polyvinyl potassium sulfate as anion type (PVSK) and Toluidine Blue (TB) as cation type in colloidal titration. TB changes its color from blue to red violet upon reacting with PVSK. This phenomenon is, however, greatly affected by salts, though not affected by sugar or glycerol (Shinkagaku Jikkenkouza 9, Bunseki Kagaku (II) 1977).

Under the circumstances, we, the inventors of this invention, have done a great deal of research work and found that the change in color of dye which results from metachromasy under the influence of salts can be utilized for determining indirectly the ionic strength or specific gravity of an aqueous solution containing it.

The change in color of a dye which results from metachromasy is not due to a change in pH of an aqueous solution containing it. Therefore, the measurement of ionic strength or specific gravity of a liquid specimen which is carried out by employing the composition of this invention is hardly affected by the pH of the specimen.

BEST MODE OF CARRYING OUT THE INVENTION

The invention will be described in further detail with reference to examples.

EXAMPLES 1 to 3

Preparation of Compositions of this Invention

The compositions of this invention as shown below were prepared by dissolving the respective components in purified water. % means weight/volume %, otherwise specified.

EXAMPLE 1

Sodium heparinate—1%
Methylene Blue—1 mM

EXAMPLE 2

Sodium dextran sulfate (Mw: 8000)—1%
Safranine O—1 mM

EXAMPLE 3

Sodium chondroitin sulfate—1%
Nile Blue—1 mM

EXAMPLES 4 to 6

Preparation of Test Pieces of this Invention

EXAMPLE 4

Figure 1:
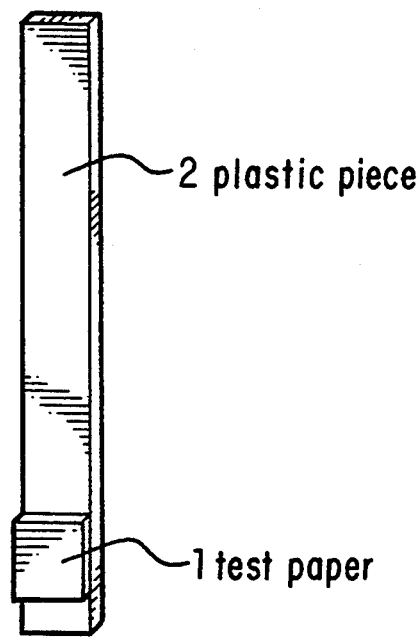
FIG. 1 is a perspective view of a test piece embodying this invention.

Filter paper (product of Toppan Shoji, 51A) was impregnated with the composition of EXAMPLE 1, dried, and cut to a size of 5×5 mm to prepare a piece of test paper 1. The test paper 1 was stuck to a plastic piece 2 having a size of 5×40 mm, whereby a test piece embodying this invention was prepared, as shown in FIG. 1.

EXAMPLE 5

A test piece embodying this invention was prepared by repeating EXAMPLE 4, except for the use of the composition of EXAMPLE 2.

EXAMPLE 6

A test piece embodying this invention was prepared by repeating EXAMPLE 4, except for the use of the composition of EXAMPLE 3.

EXAMPLES 7 to 9

Measurements with the Test Pieces of this Invention

EXAMPLE 7

Measurement 1 of Specific Gravity of Urine Specimen

Figure 2:
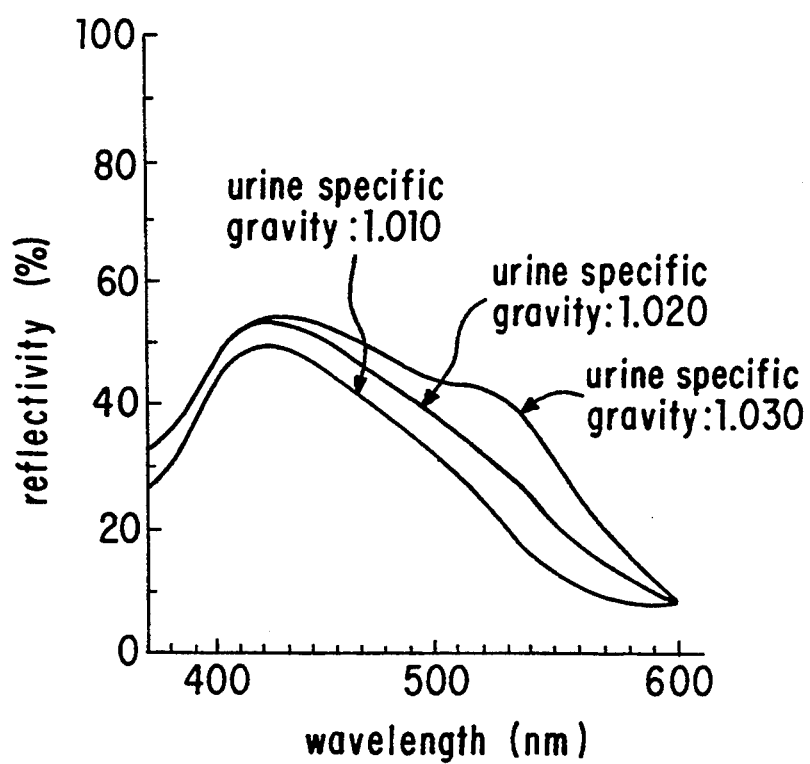
FIG. 2 is a graph showing the relation between the reflexivity and the wavelength of a color analyzer as measured of urine specimens by employing the test pieces of this invention.

The test pieces according to EXAMPLE 4 were dipped for one or two seconds in a number of urine specimens differing form one another in specific gravity, respectively, and the reflectivity thereof was measured by color analyzer TC-1800M. The results are shown in FIG. 2. As is obvious from FIG. 2, the difference in specific gravity gave a difference in color from room one specimen of urine to another.

EXAMPLE 8

Measurement 2 of Specific Gravity of Urine Specimens

The reflectivity of each of urine specimens having different specific gravities was measured by repeating EXAMPLE 7, except for the use of test pieces according to EXAMPLE 6, and was employed for calculating the K/S function thereof at 680 nm by equation I:

$$K/S = (1-R)^2/2R$$

(where $K$ = absorption coefficient, $S$ = scattering coefficient, and $R$ = reflectivity).

Figure 3:
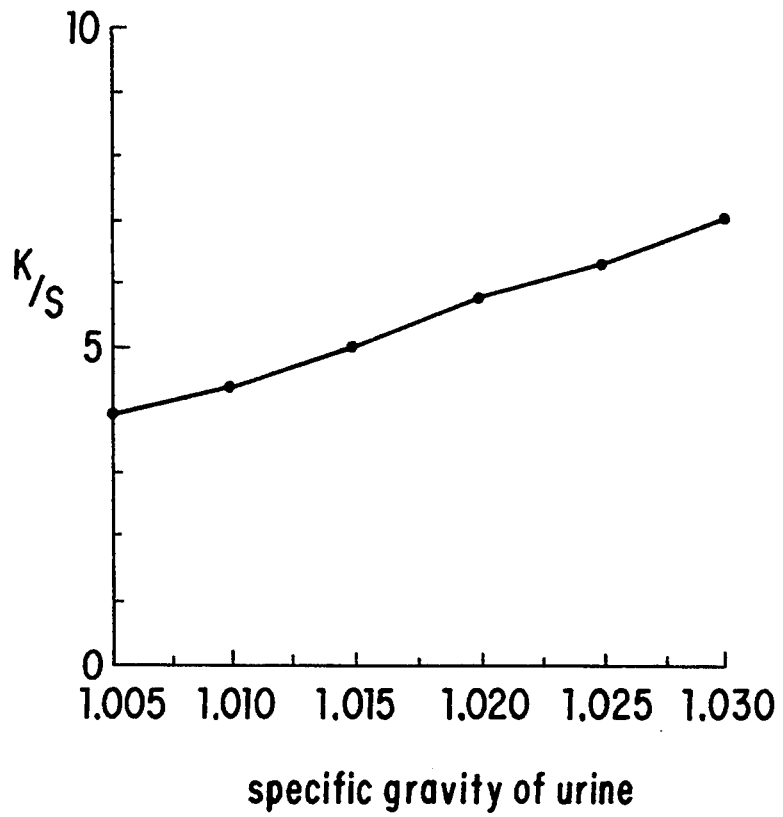
FIG. 3 is a graph showing the K/S function as measured of urine specimens by employing the test pieces of this invention in relation to their specific gravity.

The K/S function was theoretically derived from R to determine the reflectivity of a coated surface, or a woven fabric. The K/S function as calculated was proportional to the specific gravity of urine, as shown in FIG. 3.

EXAMPLE 9

Measurement 3 of Specific Gravity of Urine Specimen Specimens (Having Different pH Values)

Test pieces according to EXAMPLE 6 were dipped for one or two seconds in urine specimens (1) to (3) as described below, respectively, and the reflectivity thereof was measured by a color analyzer, TC-1800M. The K/S function at 680 nm, was determined from FIG. 3. The specific gravity of each of urine specimens (1) to (3) was also measured by a refractometer.

Urine specimen (1): Having a pH 5, and a specific gravity of 1,020 as measured by the refractometer;
Urine specimen (2): Having a pH 6, and a specific gravity of 1.020 as measured by the refractometer;
Urine specimen (3): Having a pH 7, and a specific gravity of 1.020 as measured by refractometer.

All of urine specimens (1) to (3) showed a specific gravity of 1.020 as measured by employing the test pieces of this invention, and their difference in pH did not give any difference in specific gravity.

EXAMPLE 10

Figure 4:
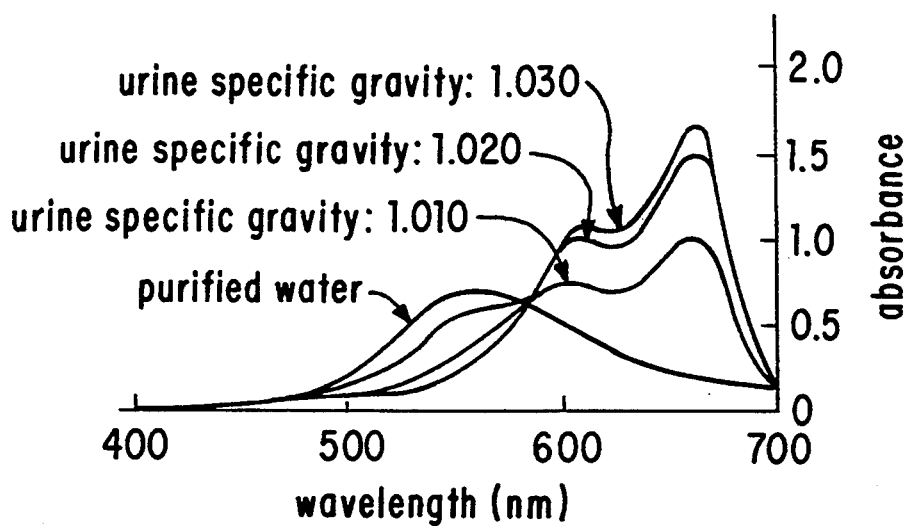
FIG. 4 is a graph showing the relation between the absorbance and the wavelength of a spectrophotometer as measured of urine specimens by employing the composition of this invention.

Measurement of specific Gravity of Urine Specimens by the Composition of this Invention 250 μl of each of a number of urine specimens having different specific gravities was added to, and mixed thoroughly in an aqueous solution of a composition embodying this invention which consisted of 3 ml of purified water, 50 μl of 1% aqueous solution of sodium dextran sulfate and 50 μl of 1 nM aqueous solution of Methylene Blue, and absorption curves were obtained by employing a Hitachi 200-20 spectrophotometer. The results are shown in FIG. 4. It is obvious from FIG. 4 that the difference in specific gravity gives different forms of absorbance can be utilized for measuring the specific gravity of such a specimen.

INDUSTRIAL UTILITY

The composition of this invention, which comprises an anionic reagent of the inonically associable type and a cationic reagent of the inonically associable type, and further contains a pH buffer agent, if required, develops a color by the association of ions, and can be used to measure the ionic strength or specific gravity of a liquid specimen without regard to the characteristics of the specimen, such as its pH and temperature. As there are a wide variety of such anionic and cationic reagents, and as they are commercially available, it is possible to obtain a wide variety of combinations of reagents and easily choose the optimum composition for a particular purpose.

The test piece of this invention is easy to prepare in a variety of forms, is simple in construction, small in size and light in weight, and is, therefore, very easy to use, carry and store, while is can be prepared at a low cost.

I claim:

1. A method for measuring ionic strength or specific gravity of a liquid specimen making use of a relationship between (a) at least one of the ionic strength and the specific gravity and (b) the color of a solution containing an anionic ion-associable reagent and a cationic ion-associable reagent, wherein the color is based on the ion-association of the reagents, which is influenced by salts of said liquid specimen, said method comprising the steps of:

preparing a solution of a composition comprising an anionic ion-associable test reagent and a cationic ion-associable reagent, and optionally containing a pH buffer agent;

adding a liquid specimen to be measured to said solution;

measuring absorbance of said solution; and calculating the ionic strength or the specific gravity of said liquid specimen by using said relationship.

2. A method as set forth in claim 1, wherein said anionic reagent is a polymer, or chain compound having a sulfonate, sulfate or phosphate ester group.

3. A method as set forth in claim 1, wherein said cationic reagent is basic dye.

4. A method as set forth in claim 3, wherein said basic dye is selected from the group consisting of thiazine, oxazine, azine, triphenylmethane, diphenylmethane, azo, indoaniline and aminoindophenol dyes.

5. A method as set forth in claim 1, wherein said pH buffer agent maintains the pH of said solution in a range of 5 to 10.

6. A method for measuring ionic strength or specific gravity of a liquid specimen making use of a relationship between (a) at least one of the ionic strength and the specific gravity and (b) the color of a test piece formed by an absorptive carrier impregnated with a composition containing an anionic ion-associable reagent and a cationic ion-associable reagent, wherein the color is based on the ion-association of the reagents, which is influenced by salts of said liquid specimen, said method comprising the steps of:

preparing a test piece by impregnating it with a solution of the composition comprising an anionic ion-associable test reagent and a cationic ion-associable reagent, and optionally containing a pH buffer agent;

contacting said test piece with a liquid specimen to be measured; and measuring the ionic strength or the specific gravity of said liquid specimen using the color change of said test piece based on said relationship.

* * * * *

UNITED STATES PATENT AND TRADEMARK OFFICE
CERTIFICATE OF CORRECTION

PATENT NO. : 5,443,990
DATED : August 22, 1995
INVENTOR(S) : Mieko Harako

It is certified that error appears in the above-indentified patent and that said Letters Patent is hereby corrected as shown below:

On the title page, item [86] PCT No.: "PCT/JP92/80459" should read --PCT/JP92/00459--

Signed and Sealed this

Twelfth Day of December, 1995

Attest:

BRUCE LEHMAN

Attesting Officer     Commissioner of Patents and Trademarks